(12) United States Patent
Sundstrom et al.

(10) Patent No.: US 10,106,790 B2
(45) Date of Patent: Oct. 23, 2018

(54) **INTERGENIC RNAS AND METHODS FOR MODULATING GENE EXPRESSION AND PATHOGENESIS IN *CANDIDA***

(71) Applicant: Trustees of Dartmouth College, Hanover, NH (US)

(72) Inventors: Paula R. Sundstrom, Lebanon, NH (US); Samin Kim, Norwich, VT (US); Quoc Bao Nguyen, Ho Chi Minh (VN)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/513,312

(22) PCT Filed: Sep. 18, 2015

(86) PCT No.: PCT/US2015/050869
§ 371 (c)(1),
(2) Date: Mar. 22, 2017

(87) PCT Pub. No.: WO2016/048813
PCT Pub. Date: Mar. 31, 2016

(65) Prior Publication Data
US 2017/0298349 A1    Oct. 19, 2017

Related U.S. Application Data

(60) Provisional application No. 62/053,372, filed on Sep. 22, 2014.

(51) Int. Cl.
| | |
|---|---|
| *C12N 15/11* | (2006.01) |
| *A61K 48/00* | (2006.01) |
| *C12N 15/113* | (2010.01) |
| *C07K 14/40* | (2006.01) |
| *C12N 15/63* | (2006.01) |
| *C12N 15/67* | (2006.01) |
| *C12N 15/00* | (2006.01) |

(52) U.S. Cl.
CPC .............. *C12N 15/11* (2013.01); *A61K 48/00* (2013.01); *C07K 14/40* (2013.01); *C12N 15/113* (2013.01); *C12N 15/63* (2013.01); *C12N 15/67* (2013.01); *C12N 15/00* (2013.01); *C12N 2310/111* (2013.01); *C12N 2310/113* (2013.01); *C12N 2310/14* (2013.01); *C12N 2310/315* (2013.01); *C12N 2310/341* (2013.01)

(58) Field of Classification Search
None
See application file for complete search history.

(56) References Cited

U.S. PATENT DOCUMENTS

| | | | |
|---|---|---|---|
| 7,241,613 B1 | 6/2007 | Willins et al. | ............. 435/255.4 |
| 2003/0124134 A1* | 7/2003 | Edwards, Jr. | ...... A61K 39/0002 |
| | | | 424/184.1 |
| 2005/0244861 A1 | 11/2005 | Sundstrom | ........................ 435/6 |
| 2014/0004154 A1 | 1/2014 | Pascolo | ..................... 424/278.1 |

FOREIGN PATENT DOCUMENTS

WO    WO 2001/38550 A2 *   5/2001    ............. C12N 15/81

OTHER PUBLICATIONS

Blankenship & Mitchell "How to build a biofilm: a fungal perspective" (2006) *Curr. Opin. Microbiol.* 9:588-94.
Candevir, et al. "Invasive Device-Associated Nosocomial Infections of a Teaching Hospital in Turkey, Four Years Experience" (2011) *Turk. J. Med. Sci.* 41:137-147.
Chandra, et al. "Biofilm formation by the fungal pathogen *Candida albicans*: development, architecture, and drug resistance" (2001) *J. Bacteriol.* 183:5385-94.
Evci, et al. "Comparative evaluation of the antifungal susceptibility of *Candida* isolates from blood specimens: results of a study in a tertiary care hospital in Bursa" (2010) Turk. J. Med. Sci. 40:141-9.
Garcia-Sanchez, et al. "*Candida albicans* biofilms: a developmental state associated with specific and stable gene expression patterns" (2004) *Eukaryot. Cell* 3:536-45.
Granger, et al. "Yeast wall protein 1 of *Candida albicans*" (2005) *Microbiology* 151:1631-44.
Green, et al. "RT-PCR Detection of *Candida albicans* ALS Gene Expression in the Reconstituted Human Epithelium (RHE) Model of Oral Candidiasis and in Model Biofilms" (2004) *Microbiology* 150:267-76.
Hazen & Howell (2003) *Manual of Clinical Microbiology*, Murray et al. (eds), 8$^{th}$ Ed. Washington DC: ASM Press, pp. 1693-1711.
Hoyer, et al. "*Candida albicans* ALS3 and insights into the nature of the ALS gene family" (1998) *Curr. Genet.* 33:451-9.
Hoyer, et al. "The ALS gene family of *Candida albicans*" (2001) *Trends Microbiol.* 9:176-80.
Kim, et al. "A 368-base-pair cis-acting HWP1 promoter region, HCR, of *Candida albicans* confers hypha-specific gene regulation and binds architectural transcription factors Nhp6 and Gcf1p" (2007) *Eukaryot. Cell* 6(4):693-709).
Kumamoto & Vinces "Alternative *Candida albicans* lifestyles: growth on surfaces" (2005) *Annu. Rev. Microbiol.* 59:113-33.
Nailis, et al. "Development and Evaluation of Different Normalization Strategies for Gene Expression Studies in *Candida albicans* biofilms by Real-time PCR" (2006) *BMC Mol. Biol.* 4:25.
O'Connor, et al. "Quantification of ALS1 gene expression in *Candida albicans* biofilms by RT-PCR using hybridisation probes on the LightCycler" (2005) *Mol. Cell Probes* 19:153-62.
Richard, et al. "*Candida albicans* biofilm—defective mutants" (2005) *Eukaryot. Cell* 4:1493-502.

(Continued)

Primary Examiner — Ekaterina Poliakova-Georgantas
(74) Attorney, Agent, or Firm — Licata & Tyrrell P.C.

(57) ABSTRACT

Intergenic non-coding RNA molecules that regulate the expression of HWP1 and ALS3 of *Candida* are provided as are methods of using the non-coding RNA molecules and complementary molecules thereof in modulating HWP1 or ALS3 expression; adherence, yeast-to-hyphal transition, or biofilm development of *Candida*; and preventing or treating candidiasis.

1 Claim, No Drawings

Specification includes a Sequence Listing.

(56) References Cited

OTHER PUBLICATIONS

Sellam et al. "Experimental annotation of the huma pathogen *Candida albicans* coding and noncoding transcribed regions using high-resolution tiling arrays" Genome Biology 2010 11:R71.
Seneviratne, et al. "Biofilm lifestyle of *Candida*: a mini review" (2008) *Oral Dis.* 14:582-90.
Shim et al. "Efficient and targeted delivery of siRNA in vivo" FEBS Journal 2010 277:4814-4827.
Staab, et al. "Expression of transglutaminase substrate activity on *Candida albicans* germ tubes through a coiled, disulfide-bonded N-terminal domain of Hwp1 requires C-terminal glycosylphosphatidylinositol modification" (2004) *J. Biol. Chem.* 279:40737-47.
Staab, et al. "Adhesive and mammalian transglutaminase substrate properties of *Candida albicans* Hwp1" (1999) *Science* 283:1535-8.
Sunstrom "Adhesion in *Candida* spp" (2002) *Cell Microbiol.* 4:461-9.
International Search Report and Written Opinion in PCT/US 15/50869 dated Jan. 22, 2016.
International Preliminary Examination Report in PCT/US 15/50869 dated Mar. 28, 2017.

\* cited by examiner

SEQUENCE LISTING

```
<160> NUMBER OF SEQ ID NOS: 17
<210> SEQ ID NO 1
<211> LENGTH: 48
<212> TYPE: DNA
<213> ORGANISM: Candida albicans

<400> SEQUENCE: 1
tatgaacaat tgaaaaaaaa aggaaatgaa aaggtaagag ttgcctaa              48

<210> SEQ ID NO 2
<211> LENGTH: 55
<212> TYPE: DNA
<213> ORGANISM: Candida albicans

<400> SEQUENCE: 2
agtccactaa ttccatcaat aaaatagatt agtgtattgt tctcttcagt acaat      55

<210> SEQ ID NO 3
<211> LENGTH: 61
<212> TYPE: DNA
<213> ORGANISM: Candida albicans

<400> SEQUENCE: 3
aacttctatt gatgatagaa cccattgcaa aaacggtatg caattgagat gcttgtgttg 60
t                                                                 61
```

```
<210> SEQ ID NO 4
<211> LENGTH: 56
<212> TYPE: DNA
<213> ORGANISM: Candida albicans

<400> SEQUENCE: 4
cacgggaaat atgaggatcc ataataagac aaaaataaaa agaacaacaa aattat        56

<210> SEQ ID NO 5
<211> LENGTH: 57
<212> TYPE: DNA
<213> ORGANISM: Candida albicans

<400> SEQUENCE: 5
taaagtacga tatcaaagaa tcataacttt gctttctatt tgataacccg cctcaaa       57

<210> SEQ ID NO 6
<211> LENGTH: 60
<212> TYPE: DNA
<213> ORGANISM: Candida albicans

<400> SEQUENCE: 6
catcttccgc ttaggtcgct ggttgcccac tttttgatgt tagtaacgtc aattatgcaa    60

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(4)
<223> OTHER INFORMATION: n is a, c, u, or g
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 7
nnnnutaggc aactcuuacc                                                20

<210> SEQ ID NO 8
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 8
uauugatgga attaguggac                                                20
```

```
<210> SEQ ID NO 9
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 9
cugaagagaa caatacacua                                              20

<210> SEQ ID NO 10
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 10
ugcaatgggt tctatcauca                                              20

<210> SEQ ID NO 11
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: misc_feature
<222> LOCATION: (1)..(2)
<223> OTHER INFORMATION: n is a, c, u, or g
<220> FEATURE:
<221> NAME/KEY: modified_base
<222> LOCATION: (16)..(20)
<223> OTHER INFORMATION: 2'-O-Methyl RNA base

<400> SEQUENCE: 11
nnacaacaca agcatcucaa                                              20

<210> SEQ ID NO 12
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
```

<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 12
auggatcctc atattucccg                                           20

<210> SEQ ID NO 13
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: misc_feature
<222> LOCATION: (1)..(5)
<223> OTHER INFORMATION: n is a, c, u, or g
<220> FEATURE:
<221> NAME/KEY: misc_feature
<222> LOCATION: (6)..(6)
<223> OTHER INFORMATION: n is a, c, t, or g
<220> FEATURE:
<221> NAME/KEY: modified_base
<222> LOCATION: (16)..(20)
<223> OTHER INFORMATION: 2'-O-Methyl RNA base

<400> SEQUENCE: 13
nnnnnntttg aggcggguua                                           20

<210> SEQ ID NO 14
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

<400> SEQUENCE: 14
gcauaattga cgttacuaac                                           20

<210> SEQ ID NO 15
<211> LENGTH: 20
<212> TYPE: DNA
<213> ORGANISM: Candida albicans
<220> FEATURE:
<221> NAME/KEY: modified_base
<222> LOCATION: (1)..(5)
<223> OTHER INFORMATION: 2'-O-Methyl RNA base
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (16)..(20)
<223> OTHER INFORMATION: 2'-O-Methyl RNA base

```
<400> SEQUENCE: 15
caaccagcga cctaagcgga                                          20

<210> SEQ ID NO 16
<211> LENGTH: 19
<212> TYPE: DNA
<213> ORGANISM: Candida albicans

<400> SEQUENCE: 16
acggtatgca attgagatg                                           19

<210> SEQ ID NO 17
<211> LENGTH: 19
<212> TYPE: DNA
<213> ORGANISM: Candida albicans

<400> SEQUENCE: 17
gcaattgaga tgcttgtgt                                           19
```

INTERGENIC RNAS AND METHODS FOR MODULATING GENE EXPRESSION AND PATHOGENESIS IN *CANDIDA*

This patent application is the National Stage of International Application No. PCT/US2015/050869 filed Sep. 18, 2015, which claims the benefit of priority from U.S. Provisional Ser. No. 62/053,372 filed Sep. 22, 2014, the teachings of each of which are herein incorporated by reference in their entirety.

INTRODUCTION

This invention was made with government support under grant number R01 AI46608 awarded by the National Institutes of Health. The government has certain rights in the invention.

BACKGROUND

*Candida* species are a commonly seen form of yeast present in the gastrointestinal tract, mucosa, and skin of healthy individuals as a part of normal flora. When the immune defense of a host is deteriorated, *Candida* spp. can cause life-threatening disorders by invading tissues. *Candida albicans* is the most commonly isolated species of nearly all forms of candidiasis (Hazen & Howell (2003) *Manual of Clinical Microbiology*, Murray et al. (eds), 8$^{th}$ Ed. Washington D.C.: ASM Press, pp 1693-711).

Biofilm formation plays an essential role in the pathogenicity of *C. albicans* (Seneviratne, et al. (2008) *Oral Dis.* 14:582-90; Richard, et al. (2005) *Eukaryot. Cell* 4:1493-502). Biofilm is a cell population that is surrounded by an extracellular matrix composed of yeast cells and filaments; it has a relationship with the surface and exhibits different phenotypic features than planktonic cells (Blankenship & Mitchell (2006) *Curr. Opin. Microbiol.* 9:588-94). This cell population behaves as a continuous reservoir in the spread of infection. Additionally, it is resistant to many antifungal agents, as compared to planktonic cells (Seneviratne, et al. (2008) supra; Richard, et al. (2005) supra). The initiation of biofilm formation is dependent on the attachment of yeast cells to a substrate, which is followed by the attachment of yeast cells to each other (Granger, et al. (2005) *Microbiology* 151:1631-44). Adherence must extend to the hyphal layers. The agglutinin-like sequence (ALS) gene family is the largest family among known adhesins in *C. albicans* (Hoyer, et al. (1998) *Curr. Genet.* 33:451-9). It is known that ALS family members interact with several substrates, including host cells and proteins (Hoyer, et al. (2001) *Trends Microbiol.* 9:176-80; Sunstrom (2002) *Cell Microbiol.* 4:461-9; Kumamoto & Vinces (2005) *Annu. Rev. Microbiol.* 59:113-33). The finding that expression of ALS1 and other family members increases during biofilm development in vitro suggested that the ALS family plays a role in biofilm formation (Chandra, et al. (2001) *J. Bacteriol.* 183:5385-94; Green, et al. (2004) *Microbiology* 150:267-76; O'Connor, et al. (2005) *Mol. Cell Probes* 19:153-62). Hyphal wall protein 1 (HWP1), another adhesion gene, is also upregulated during biofilm development (Garcia-Sanchez, et al. (2004) *Eukaryot. Cell* 3:536-45). HWP1, a glycosylphosphatidylinositol-linked mannoprotein like the ALS proteins, is the best-characterized hyphal adhesin (Sundstrom (2002) supra; Staab, et al. (2004) *J. Biol. Chem.* 279:40737-47). It is a substrate for transglutaminase activity derived from a host, and thus it mediates covalent attachment of *C. albicans* to host cells (Sundstrom (2002) supra; Staab, et al. (1999) *Science* 283:1535-8).

The regulation of morphology-specific gene expression is a poorly understood process that is critical for the ability of *C. albicans* to adapt to and invade human hosts. However, a 368-bp region of the HWP1 promoter, designated the HWP1 control region (HCR), has been shown to be critical for activation under hypha-inducing conditions and confer developmental regulation to a heterologous ENO1 promoter (Kim, et al. (2007) *Eukaryot. Cell* 6(4):693-709).

Although there are many studies in the literature investigating pathogenic *Candida*, antifungal resistance, and virulence factors of *Candida* (Richard, et al. (2005) supra; Hoyer, et al. (1998) supra; Green, et al. (2004) supra; Hailis, et al. (2006) *BMC Mol. Biol.* 4:25; Candevir, et al. (2011) *Turk. J. Med. Sci.* 41:137-147; Evci, et al. (2010) *Turk. J. Med. Sci.* 40:141-9), new targets and approaches toward preventing or managing oral candidiasis are needed.

SUMMARY OF THE INVENTION

This invention is an intergenic non-coding RNA (ncRNA) having the nucleotide sequence of SEQ ID NO:1, SEQ ID NO:2, SEQ ID NO:3, SEQ ID NO:4, SEQ ID NO:5 or SEQ ID NO:6; or a nucleic acid molecule having a nucleotide sequence complementary thereto, e.g., an antisense or siRNA molecule. In some embodiments, the ncRNA molecule or ncRNA complement is in a recombinant vector, e.g., an expression vector. Methods for modulating the expression of HWP1 or ALS3; modulating adherence, yeast-to-hyphal transition, and/or biofilm development of *Candida*; and preventing or treating candidiasis using the ncRNA molecule or ncRNA complement are also provided.

DETAILED DESCRIPTION OF THE INVENTION

It has now been found that the morphology-specific regulation of HWP1 and ALS3 gene expression involves intergenic RNAs. In particular, it has been demonstrated that the HWP1 control region (HCR) is essential for coupling HWP1 expression and Hwp1 protein deposition during the initiation stage of germ tube formation. In a *C. albicans* strain lacking HCR, Hwp1 protein is not present on emerging germ tubes, whereas in the wild-type strain, Hwp1 protein is present on 100% of emerging germ tubes. Furthermore, it was observed that in a *C. albicans* strain lacking HCR, the expression of Hwp1 during germ tube elongation was variable among germ tubes in the same population. This variability in Hwp1 was similar to that of FLO11 in *Saccharomyces cerevisiae* (Bumgarner, et al. (2012) *Mol. Cell* 45:470-82), which is regulated by long intergenic noncoding RNAs (ncRNAs). Accordingly, it was determined whether Hwp1 and another hypha-specific gene, ALS3, were regulated by intergenic RNAs. The results of this analysis indicated the presence of multiple intergenic RNAs of relevance to repression of Hwp1 and Als3 in yeast growth conditions and activation of Hwp1 and Als3 in hyphal growth conditions. To demonstrate the importance of intergenic transcripts in regulation of HWP1, transcriptional termination experiments were performed using *C. albicans* termination and control sequences. The results of this analysis indicated that the intergenic RNAs described herein exert their effects on HWP1 and ALS3 via a cis-acting process. This newly identified process in *Candida* involving the transcription of co-regulated hypha-specific genes can now be used as a target for interfering with pathogenic mechanisms and preventing or treating candidiasis.

Accordingly, the present invention provides intergenic ncRNA and use thereof for modulating gene regulation during morphogenesis and hence pathogenicity of *Candida*. "Non-coding RNAs," or "ncRNAs," are widely variable in length and have been found to be involved in gene regulation. Based on ncRNA length, regulatory ncRNA can be divided into at least three groups: short ncRNA including microRNA (miRNA, 22-23 nucleotides) and piwi-interacting RNA (piRNA, 26-31 nucleotides); medium ncRNA (50-200 nucleotides); and long ncRNA (>200 nucleotides). In some embodiments, a ncRNA molecule of the invention is a long ncRNA of between 200 and 10000 nucleotides, 200 and 5000 nucleotides or 200 and 1000 nucleotides in length. In particular embodiments, a ncRNA molecule of the invention is a long ncRNA having a 5' sequence as provided in SEQ ID NO:1, SEQ ID NO:2, SEQ ID NO:3, SEQ ID NO:4, SEQ ID NO:5, or SEQ ID NO:6 (Table 1).

TABLE 1

| Intergenic RNA | Sequence of 5' End | SEQ ID NO: |
|---|---|---|
| HWP1 | | |
| HCR-Y (Yeast-specific) | 5'-TAT GAA CAA TTG AAA AAA AAA GGA AAT GAA AAG GTA AGA GTT GCC TAA-3' | 1 |
| HWP1-H (Hypha-specific) | 5'-AGT CCA CTA ATT CCA TCA ATA AAA TAG ATT AGT GTA TTG TTC TCT TCA GTA CAA T-3' | 2 |
| ALS3 | | |
| ALS3-Y (Yeast-specific) | 5'-AAC TTC TAT TGA TGA TAG AAC CCA TTG CAA AAA CGG TAT GCA ATT GAG ATG CTT GTG TTG T-3' | 3 |
| ALS3-H1 (Hypha-specific) | 5'-CAC GGG AAA TAT GAG GAT CCA TAA TAA GAC AAA AAT AAA AAG AAC AAC AAA ATT AT-3' | 4 |
| ALS3-H2 (Hypha-specific) | 5'-TAA AGT ACG ATA TCA AAG AAT CAT AAC TTT GCT TTC TAT TTG ATA ACC CGC CTC AAA-3' | 5 |
| ALS3-H3 (Hypha-specific) | 5'-CAT CTT CCG CTT AGG TCG CTG GTT GCC CAC TTT TTG ATG TTA GTA ACG TCA ATT ATG CAA-3' | 6 |

Not wishing to be bound by theory, the transcription of an ncRNA described herein, in one aspect, may be initiated far upstream from the HWP1 or ALS3 open reading frame and be transcribed across much of the promoter of HWP1 or ALS3, thereby repressing HWP1 or ALS3 transcription in cis. This supports a "promoter occlusion" model (Martens, et al. (2004) *Nature* 429:571-4; Hongay, et al. (2006) *Cell* 127:735-74), in which transcription of HCR-Y or ALS3-Y blocks access to general transcription factors and to chromatin remodelers required for nucleosome ejection. The HWP1-H or ALS3-H1/ALS3-H2/ALS3-H3 ncRNA is transcribed from the non-coding strand of HCR-Y or ALS3-Y, respectively, and promotes HWP1 or ALS3 transcription by interfering with HCR-Y or ALS3-Y. This aspect would be similar that observed with FLO11. However, in the instant case, all of the RNA's both coding and non-coding for HWP1 and ALS3 are transcribed from the same strand. While the presence of HCR-Y and ALS3-Y support a promoter occlusion model, HWP1-H and ALS3-H1/ALS3-H2/ALS3-H3 are likely to be important for dismantling TUP1-mediated repression and exposing the promoters of HWP1 and ALS3 to the transcriptional machinery. This aspect would be similar that observed with Fbp1 in *Schizosaccharomyces pombe*, wherein the Fbp1 gene is repressed by Tup11/12. See, Hirota & Ohta (2009) Epigenetics 4:5-7, in particular Figure A of this reference. In accordance with this model, the cascade of mlon ncRNA's displaces Tup11/12 leading to massive induction of the Fbp1 gene. In this case, Fbp1 is induced by glucose starvation, not morphological change, however disruption of repressive chromatin by ncRNA's is in agreement with the findings herein with respect to the mechanism of activation of HWP1 and ALS3 during the yeast to hyphal transition. The expression of non-coding Y and H RNA's is likely controlled by different transcription factors in yeast and hyphal growth conditions. Of note, the toggle switch per the FLO11 model is controlled by the random binding of transcription factors that activate either the repressive or activating ncRNA's. Accordingly, the present invention may also be of use in interfering with the mechanisms of RNA transcription, including the transcription factors that lead to the expression of the non-coding RNA's during morphogenesis.

Accordingly, the present invention provides the use of the ncRNA molecules herein as well as molecules complementary thereto for modulating the expression of HWP1 and/or ALS3; modulating adherence, yeast-to-hyphal transition, and/or biofilm development of *Candida*; and decreasing or delaying pathogenesis and infection by *Candida*. By "modulate" is meant an increase or decrease in the expression of HWP1 and/or ALS3; or repression or induction of adherence, yeast-to-hyphal transition, and/or biofilm development compared to that observed in the absence of the ncRNA molecules or complements thereof.

As used herein, the terms "complementary" or "complementarity" refer to the ability of a nucleic acid to form hydrogen bond(s) with another nucleic acid by either traditional Watson-Crick or other non-traditional types. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. Complementarity may also be "partial" in which only some of the nucleic acids' bases are matched according to the base pairing rules.

Complements of the ncRNA molecules of this invention, i.e., "ncRNA complements," are nucleic acid molecules, which have complementarity to the ncRNA molecules of the invention thereby blocking or inhibiting the activity of the ncRNA or cleaving the ncRNA and consequently modulating the expression of HWP1 or ALS3. Examples of ncRNA complements of the invention include, but are not limited, antisense molecules, siRNA, shRNA, miRNA, ribozymes, catalytic RNA, enzymatic RNA, catalytic DNA, aptazyme or aptamer-binding ribozyme, DNAzyme, or RNA enzyme. In particular embodiments, a ncRNA complement is an antisense molecule or siRNA.

An antisense molecule is a non-enzymatic nucleic acid molecule that binds to target RNA by means of RNA-RNA or RNA-DNA or RNA-PNA (protein nucleic acid; Egholm, et al. (1993) *Nature* 365:566) interactions and alters the activity of the target RNA (for a review, see Stein & Cheng (1993) *Science* 261:1004 and U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of antisense strategies, see Schmajuk, et al. (1999) *J. Biol. Chem.* 274:21783-21789; Delihas, et al.

(1997) *Nature* 15:751-753, Stein, et al. (1997) *Antisense N. A. Drug Dev.* 7:151; Crooke (2000) *Methods Enzymol.* 313:3-45; Crooke (1998) *Biotech. Genet. Eng. Rev.* 15:121-157; Crooke (1997) *Ad. Pharmacol.* 40:1-49. Antisense molecules can be designed using web-based tools such as Antisense Design (Integrated DNA Technologies). Exemplary antisense molecules that are complementary to the ncRNA of this invention are provided in Table 2.

TABLE 2

| Antisense Target | Antisense Sequence (5'→3') | SEQ ID NO: |
|---|---|---|
| HCR-Y | mNmNmNmNmUTAGGCAACTCmUmUmAmCmC | 7 |
| HWP1-H | mUmAmUmUmGATGGAATTAGmUmGmGmAmC | 8 |
| HWP1-H | mCmUmGmAmAGAGAACAATAmCmAmCmUmA | 9 |
| ALS3-Y | mUmGmCmAmATGGGTTCTATmCmAmUmCmA | 10 |
| ALS3-Y | mNmNmAmCmAACACAAGCATmCmUmCmAmA | 11 |
| ALS3-H1 | mAmUmGmGmATOCTCATATTmUmCmCmCmG | 12 |
| ALS3-H2 | mNmNmNmNmNNTTTGAGGCGmGmGmUmUmA | 13 |
| ALS3-H3 | mGmCmAmUmAATTGACGTTAmCmUmAmAmC | 14 |
| ALS3-H3 | mCmAmAmCmCAGCGACCTAAmGmCmGmGmA | 15 |

Oligos are 20 bases in length with five 2'-O-Methyl RNA bases flanking the 3' and 5' ends with an all phosphorothioate backbone.

The term "siRNA" or "short interfering RNA" as used herein refers to a double-stranded nucleic acid molecule capable of RNA interference "RNAi." See, for example, Bass (2001) *Nature* 411:428-429; Elbashir, et al. (2001) *Nature* 411:494-498; WO 00/44895; WO 01/36646; WO 99/32619; WO 00/01846; WO 01/29058; WO 99/07409; and WO 00/44914. In a particular embodiment, the siRNA molecule of the invention is a double-stranded RNA, wherein one strand of the RNA is complementary to a ncRNA molecule of this invention. In another embodiment, a siRNA molecule of the invention is a double-stranded RNA wherein both strands of RNA are connected by a non-nucleotide linker. Alternately, a siRNA molecule of the invention is a double-stranded RNA wherein both strands of RNA are connected by a nucleotide linker, such as a loop or stem loop structure. siRNA molecules of the invention are typically between about 14 and about 50 nucleotides in length. In another embodiment, a single strand component of a siRNA molecule of the invention is about 14, 15, 16, 17, 18, 19, 20, 21, 22, 23, 24, 25, 26, 27, or 28 nucleotides in length. In one embodiment, a siRNA molecule of the invention is from about 28 to about 56 nucleotides in length. In another embodiment, a siRNA molecule of the invention is about 40, 41, 42, 43, 44, 45, 46, 47, 48, 49, 50, 51, or 52 nucleotides in length. As used herein, siRNA molecules need not be limited to those molecules containing only RNA, but further encompasses chemically modified nucleotides and non-nucleotides. siRNA molecules can be designed using web-based tools such as RNAi Design (Integrated DNA Technologies) or BLOCK-IT RNAi Designer (Invitrogen). By way of illustration, an siRNA molecule targeting the ALS3-Y may have the sequence of 5'-ACG GTA TGC AAT TGA GAT G-3' (SEQ ID NO: 16) or 5'-GCA ATT GAG ATG CTT GTG T-3' (SEQ ID NO:17). See also Moazeni, et al. ((2012) *Mycopathologia* 174:177-85) for the use of RNAi technology in gene silencing in *C. albicans*.

In addition to the complementary molecules described herein, the intergenic ncRNAs of this invention can also be used in screening assays to identify other agents, e.g., small molecules, for use in modulating the expression of HWP1 and/or ALS3. Moreover, the ncRNAs can also be used in the elucidation of a general mechanism of regulation of the ncRNA's. Although the sequences of the ncRNA's are gene-specific, there is likely to be an overall mechanism that involves transcription factors that are either expressed or post-translationally modified by a common process during morphological transitions that would control sets of non-coding RNA's to coordinately regulate their expression. In this regard, this general mechanism of control could be inhibited by a single inhibitory agent, rather than needing a host of specific intergenic RNA's.

The ncRNA molecules and ncRNA complements can be synthesized chemically or expressed via the use of a single stranded DNA expression vector or equivalent thereof. Accordingly, this invention also includes recombinant vectors harboring the nucleic acid molecules of this invention. In particular embodiments, the recombinant vector is an expression vector that includes the appropriate regulatory sequences (e.g., a promoter and terminator) for expressing the nucleic acid molecules of this invention.

In accordance with the foregoing, the ncRNA molecule, ncRNA complement or expression vector are used in methods for modulating the expression of HWP1 and/or ALS3 and modulating adherence, yeast-to-hyphal transition, and/or biofilm development of *Candida*. Such methods can be carried out by contacting a *Candida* cell with an effective amount of a ncRNA molecule, ncRNA complement or expression vector of the invention so that the expression of HWP1 and/or ALS3 is modulated thereby modulating adherence, yeast-to-hyphal transition, and/or biofilm development. By way of illustration, a nucleic acid molecule complementary to HWP1-H or ALS3-H1/ALS3-H2/ALS3-H3 can be provided to a *Candida* cell to maintain a *Candida* cell in a yeast state and/or reduce, inhibit or delay adherence and/or transition to the hyphal form of the *Candida*.

The term "contact," when applied to a cell, is used herein to describe the process by which a molecule or composition described herein is delivered to a target cell or is placed in direct juxtaposition with the target cell, i.e., a *Candida* cell. In any embodiment herein, a cell can be in vitro, such as a cell in culture, or in vivo within a living subject. In this respect, a ncRNA molecule, ncRNA complement or expression vector of this invention can be used directly, or can be complexed with cationic lipids, packaged within liposomes, or otherwise delivered to target cells. For in vivo delivery, an ncRNA molecule, ncRNA complement or expression vector can be locally administered to relevant tissues or through injection or infusion pump, with or without their incorporation in biopolymers.

In so far as adherence and transition from the yeast form to hyphal form are key features contributing to *Candida* infectivity and pathogenesis, the present invention also relates to methods for preventing and/or treating candidiasis in a subject using an ncRNA molecule, ncRNA complement or expression vector of the invention. Such methods involve administering to a subject in need of treatment an effective amount of an ncRNA molecule, ncRNA complement or expression vector described herein thereby inhibiting *Candida* adhesion and/or yeast-to-hyphal transition and preventing and/or treating candidiasis in the subject. In most cases the subject being treated will be a human being, but treatment of agricultural animals, e.g., livestock and poultry, and companion animals, e.g., dogs, cats and horses, is also contemplated. Moreover, the *Candida* infection being prevented or treated in most cases is *C. albicans*. However, infection by *C. tropicalis*, *C. glabrata*, *C. krusei*, *C. parapsilosis*, *C. dubliniensis* and *C. lusitaniae* can also be prevented and/or treated. The dosage or effective amount of an ncRNA molecule or ncRNA complement is an amount which achieves the desired outcome of preventing or reducing at least one sign or symptom of candidiasis.

One or more ncRNA molecules or ncRNA complements of this invention can be administered alone or in combination and be further combined with one or more known antifungal agent. Such antifungal agents include, but are not limited to amphotericin B, nystatin, clotrimazole, econazole, ketoconazole, miconazole, oxiconazole, sulconazole, butenafine HCl, naftifine, terbinafine, haloprogin, tolnaftate, and undecylenate.

To evaluate the efficacy of molecules of the invention, one of skill will appreciate that a model system of candidiasis can be utilized to evaluate the adsorption, distribution, metabolism and excretion of a compound as well as its potential toxicity in acute, sub-chronic and chronic studies.

For therapeutic use, it is generally desirable that the therapeutic agent be provided to a subject in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions appropriately formulated for parenteral (for example, by intravenous, intraperitoneal, subcutaneous or intramuscular injection), topical (including buccal and sublingual), oral, intranasal, intravaginal, or rectal administration can be prepared according to standard methods. In particular embodiments, the molecules of the invention would be administered in oral gel formulations such as those described in Aksungur, et al. ((2004) J. Control Release 98:269-79) or Buchsel (2008) Expert Opin. Drug Metab. Toxicol. 11:1449-54), wherein bioadhesive and antimicrobial properties offer the palliative effects of an occlusive dressing and the potential for delivering drugs, including anti-candidal agents.

The selected dosage level will depend upon a variety of factors including the activity of the particular ncRNA molecule or ncRNA complement employed, the route of administration, the time of administration, the rate of excretion or metabolism, the duration of the treatment, other drugs, compounds and/or materials used in combination with the particular agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of an agent at levels lower than that required in order to achieve the desired therapeutic effect and gradually increase the dosage until the desired effect is achieved.

What is claimed is:

1. A recombinant vector expressing a nucleic acid molecule consisting of:
   (a) SEQ ID NO:1, SEQ ID NO:2, SEQ ID NO:3, SEQ ID NO:4, SEQ ID NO:5 or SEQ ID NO:6; or
   (b) a nucleotide sequence complementary to a nucleotide sequence of (a).

* * * * *

UNITED STATES PATENT AND TRADEMARK OFFICE
CERTIFICATE OF CORRECTION

PATENT NO. : 10,106,790 B2
APPLICATION NO. : 15/513312
DATED : October 23, 2018
INVENTOR(S) : Sundstrom et al.

Page 1 of 1

It is certified that error appears in the above-identified patent and that said Letters Patent is hereby corrected as shown below:

In the Specification

Column 1, please delete Lines 14-17 and insert in its place the following:
--This invention was made with government support under grant number R01 AI046608 awarded by the National Institutes of Health. The government has certain rights in the invention.--

Signed and Sealed this
Twenty-eighth Day of April, 2020

Andrei Iancu
*Director of the United States Patent and Trademark Office*